(12) United States Patent
Itoh

(10) Patent No.: US 6,805,294 B2
(45) Date of Patent: Oct. 19, 2004

(54) BAR CODE GENERATING APPARATUS

(76) Inventor: Teruaki Itoh, 5-25, Kokaihommachi, Kumamoto-shi, Kumamoto-ken (JP)

( * ) Notice: Subject to any disclaimer, the term of this patent is extended or adjusted under 35 U.S.C. 154(b) by 0 days.

(21) Appl. No.: 10/689,631

(22) Filed: Oct. 22, 2003

(65) Prior Publication Data

US 2004/0084531 A1 May 6, 2004

(30) Foreign Application Priority Data

Nov. 1, 2002 (JP) ........................................ 2002-320177

(51) Int. Cl.⁷ ................................................. G06K 7/10
(52) U.S. Cl. ............................. 235/462.01; 235/462.2; 235/462.24
(58) Field of Search ......................... 235/462.01, 462.2, 235/462.24

(56) References Cited

U.S. PATENT DOCUMENTS 3,909,203 A  *  9/1975  Young et al. .................. 422/67
4,476,381 A  * 10/1984  Rubin ......................... 235/375
5,193,855 A  *  3/1993  Shamos ....................... 283/117

FOREIGN PATENT DOCUMENTS

JP            8-220105          8/1996

* cited by examiner

Primary Examiner—Thien M. Le
Assistant Examiner—Lisa M. Caputo
(74) Attorney, Agent, or Firm—Nixon & Vanderhye P.C.

(57) ABSTRACT

A bar code generating apparatus includes a specimen container holder which holds a container containing a specimen, a holder conveyance device which conveys the specimen container holder, a sensor which senses that the specimen container holder is conveyed to a specific position, a conveyance temporary stop mechanism which operates based on the information output from the sensor and temporarily stops conveyance of the specimen container holder, a rotation control mechanism which rotates the specimen container holder, which stops temporarily, on an axis of the holder, an electronic camera which picks up an image of recording information on the surface of the specimen container held by the rotated specimen container holder, and a bar-coding device which codes the recording information into a bar code based on data of the picked-up image.

8 Claims, 2 Drawing Sheets

BAR CODE GENERATING APPARATUS

CROSS-REFERENCE TO RELATED APPLICATIONS

This application is based upon and claims the benefit of priority from the prior Japanese Patent Application No. 2002-320177, filed Nov. 1, 2002, the entire contents of which are incorporated herein by reference.

BACKGROUND OF THE INVENTION

1. Field of the Invention

The present invention relates to a bar code generating apparatus for reading recording information such as patients' names from specimen containers containing a specimen such as blood and then automatically generating bar codes corresponding to the recording information.

2. Description of the Related Art

Bar code readers for automatically reading information from a bar code label attached to a specimen container such as a test tube have been known conventionally. For example, Jpn. Pat. Appln. KOKAI Publication No. 8-220105 discloses a bar code reader that is located alongside a conveyance path for conveying a specimen container holder. This bar code reader automatically reads information from a bar code label attached to the outer surface of a specimen container held by the holder and then transmits the read information to a control device (see paragraph [0023] and FIG. 2). However, there were no bar code generators for automatically reading recording information such as patients' names and then automatically generating a bar code corresponding to the read recording information in order to make a bar code label. For this reason, conventionally, an operator read recording information as described above and input it to a bar code label issuing device to make a bar code label.

BRIEF SUMMARY OF THE INVENTION

An object of the present invention is to provide a bar code generating apparatus capable of automatically, speedily, correctly generating bar codes corresponding to characters indicative of, e.g., names and handwritten information which are recorded on specimen containers such as test tubes.

In order to attain the above object, a bar code generating apparatus according to an aspect of the present invention has the following characteristic configuration. The other characteristic configurations will be clarified in the embodiment later.

A bar code generating apparatus according to an aspect of the present invention, comprises a specimen container holder which holds a container containing a specimen, a holder conveyance device provided to convey the specimen container holder, a sensor which senses information indicating that the holder conveyance device conveys the specimen container holder to a specific position and outputs the information, a conveyance temporary stop mechanism which operates based on the information output from the sensor and temporarily stops conveyance of the specimen container holder, a rotation control mechanism which rotates the specimen container holder, which is stopped temporarily by the conveyance temporary stop mechanism, on an axis of the holder, an electronic camera which picks up an image of recording information on a surface of the specimen container held by the specimen container holder rotated by the rotation control mechanism, and a bar-coding device which codes the recording information into a bar code based on data of the image picked up by the electronic camera.

DETAILED DESCRIPTION OF THE INVENTION (Embodiment)

Figure 1:
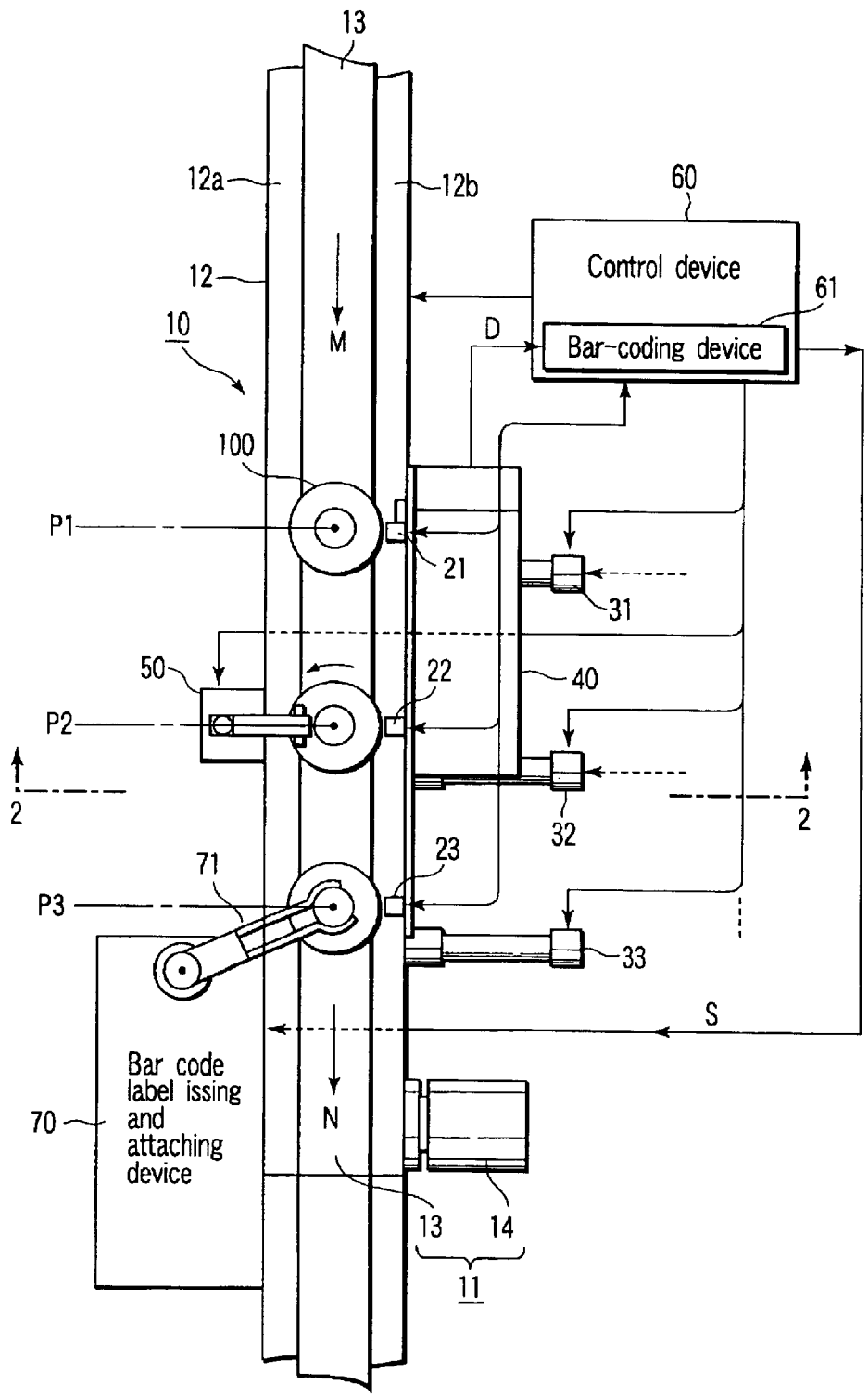
FIG. 1 is a plan view showing an outline of a specimen container conveyance system including a bar code generating apparatus according to an embodiment of the present invention.
Figure 2:
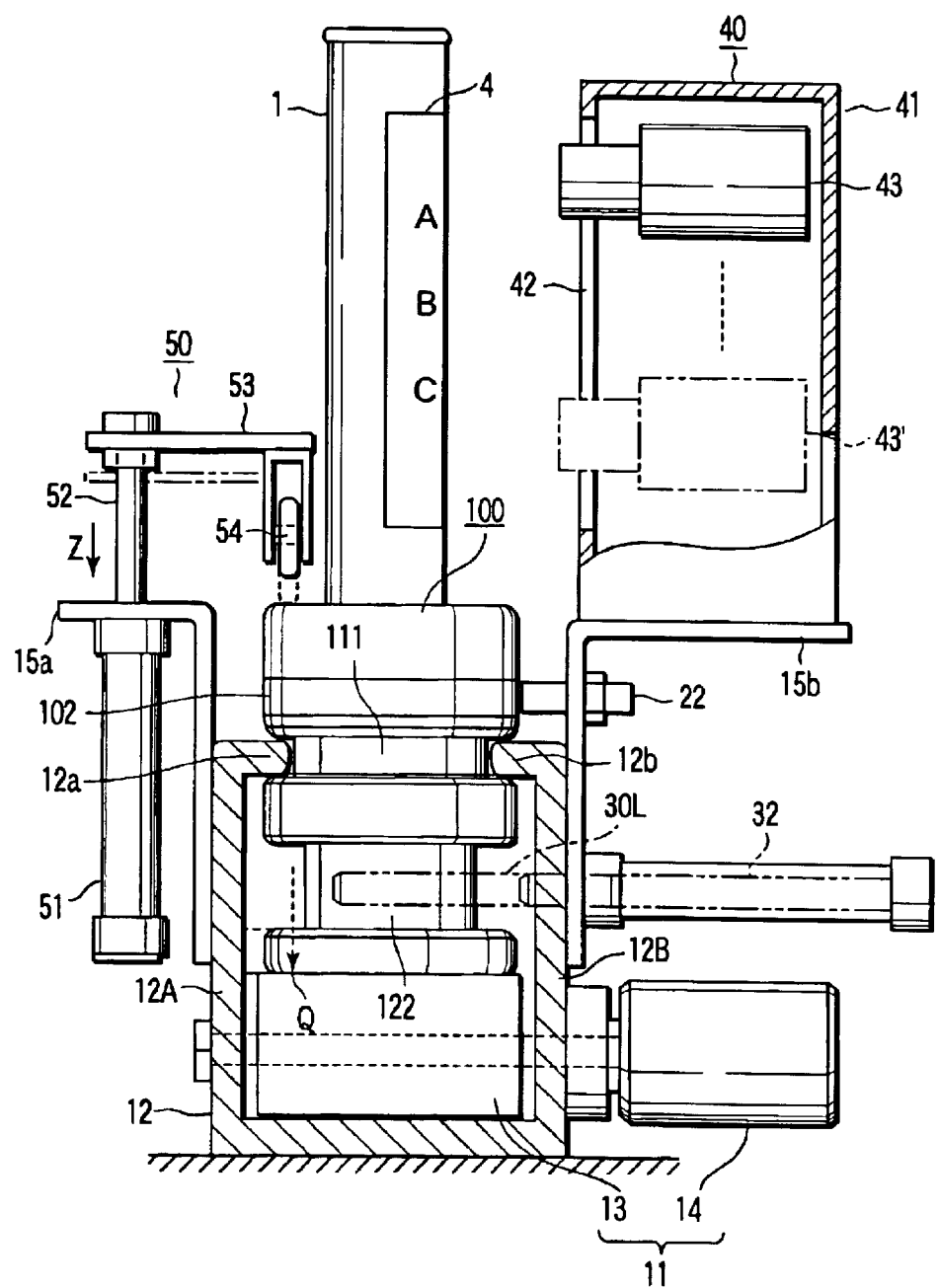
FIG. 2 is a sectional view taken along line 2—2 of FIG. 1.

In FIGS. 1 and 2, reference numeral 10 denotes a specimen container holder conveyance device including a belt conveyor mechanism 11 and a guide mechanism 12. The conveyor mechanism 11 moves an endless belt 13 made of urethane or the like by the power of a motor 14 in order to convey a specimen container holder 100 (described later). The guide mechanism 12 has sidewalls 12A and 12B formed on both sides of the conveyor mechanism 11. The sidewalls 12A and 12B have guide edge portions 12a and 12b at their upper ends. The guide edge portions 12a and 12b are fitted into a first annular groove 111 of the specimen container holder 100. The guide mechanism 12 and endless belt 13 make up a so-called conveyance lane.

Inverted L-shaped holding plates 15a and 15b are attached to the outer surfaces of the sidewalls 12A and 12B, respectively. Of the holding plates 15a and 15b, the holding plate 15b that is located on the right side of each of FIGS. 1 and 2 has holder sensors 21, 22 and 23 on its vertical portion. The sensors 21, 22 and 23 are arranged at regular intervals and each formed of a magnetically sensing type metal sensor. The sensors 21, 22 and 23 sense an iron-made labeling ring 102 of the specimen container holder 100 that has been conveyed to a specific position by the holder conveyance device 10 and then output the sensed information to a control device 60.

The holding plate 15b also has conveyance temporary stop mechanisms 31, 32 and 33 on the vertical portion. The conveyance temporary stop mechanisms 31, 32 and 33 are each configured chiefly by an air piston/cylinder device.

The control device 60 operates in response to a signal output from each of the sensors 21, 22 and 23. The conveyance temporary stop mechanisms 31, 32 and 33 are driven in response to control signals output from the control device 60. When the conveyance temporary stop mechanisms 31, 32 and 33 are driven, they project an operation rod 30L coupled to a piston section and insert it in a forward area of a second annular groove 122 of the holder 100 in the conveyance direction of the holder 100. The holder 100 therefore stops temporarily.

In the present embodiment, the conveyance temporary stop mechanisms 31, 32 and 33 operate while the endless belt 13 of the belt conveyor mechanism 11 is moving. Therefore, the specimen container holder 100 slips on the belt 13 and temporarily stops in a specific position of the belt 13.

An information reading device 40 is fixedly mounted on the horizontal portion of the holding plate 15b. The device 40 includes a housing 41 in which an electronic camera 43 is disposed to pick up an image through a window 42 of the device 40. The electronic camera 43 has a CCD (charge coupled device) as an image pickup device and moves up and down by means of a lifting/lowering control mechanism (not shown).

The information reading device 40 picks up an image of characters indicative of, e.g. names and handwritten information A, B and C on a sheet 4 attached to a specimen container 1 that is rotated by a rotation control mechanism 50 (described later), and transmits data D of the image to the control device 60.

The control device 60 includes a bar-coding device 61. The bar-coding device 61 codes the information A, B and C into bar code information S based on the data D and then supplies the bar code information S to a bar code label issuing and attaching device 70.

The bar code label issuing and attaching device 70 issues a bar code label based on the bar code information S supplied from the bar-coding device 61. The bar code label is automatically attached to the outer surface of a given specimen container 1 moved by a robot arm 71. The specimen container 1 with the bar code label is returned to the original holder by the robot arm 71.

On the other hand, the holding plate 15a that is located on the left side of each of FIGS. 1 and 2 has the rotation control mechanism 50 described above. The mechanism 50 rotates the specimen container holder 100, which is stopped temporarily by the conveyance temporary stop mechanism 32, on the axis of the holder 100. Thus, the specimen container 1 held in the holder 100 rotates such that an information recording area (an area of the sheet 4 to which a bar code label is attached) passes in front of the window 42 of the information reading device 40.

The rotation control mechanism 50 includes a driving source 51 configured by an air piston/cylinder device, an operation rod 52 coupled to the piston section of the driving source 51, and a pressing roller 54 attached to the tip of the operation rod 52 through a spring member 53. If the operation rod 52 is retracted in the direction of arrow Z, the pressing roller 54 presses an eccentric position of the top of the specimen container holder 100 that stops in a specific position. Consequently, the specimen container holder 100 generates a rotating force in association with the moving force of the belt 13.

If the eccentric position of the top of the specimen container holder 100, which slips on the belt 13 and stops in the specific position thereof by the conveyance temporary stop mechanism 32, is depressed, the holder 100 slightly inclines. Thus, the friction of an eccentric position (indicated by broken arrow Q) of the bottom of the holder 100 corresponding to that of the top of the holder 100 locally increases and accordingly the holder 100 generates a rotating force.

An operation of the bar code generating apparatus so configured will now be described. First, when the holder conveyance device 10 operates, the specimen container holder 100 containing a specimen container 1 is conveyed to position P1 in FIG. 1 by the belt conveyor mechanism 11 as indicated by arrow M.

When the specimen container holder 100 comes to position P1, the holder sensor 21 senses the labeling ring 102 of the holder 100 and transmits the sensed information to the control device 60. Then, the control device 60 sends an operation control signal to the conveyance temporary stop mechanism 31. The mechanism 31 operates to project the operation rod 30L. The holder 100 therefore slips on the moving belt 13 and stops in position P1.

Then, the holder sensor 22 confirms whether another specimen container holder is present in position P2. When the sensor 22 confirms that no other holders stop in position P2, the conveyance temporary stop mechanism 31 is reset. Accordingly, the specimen container holder 100 restarts to move from position P1. When the sensor 22 confirms that a specimen container holder other than the holder 100 is present in position P2, the holder 100 stands by in position P1 until the former holder leaves position P2.

When the specimen container holder 100 restarts to move and reaches position P2, the holder sensor 22 senses the labeling ring 102 of the holder 100 and transmits the sensed information to the control device 60. Then, the control device 60 sends an operation control signal to the conveyance temporary stop mechanism 32. The mechanism 32 operates to project the operation rod 30L. The holder 100 therefore slips on the moving belt 13 and stops in position P2.

The control device 60 issues an operation control command to the rotation control mechanism 50 and accordingly the mechanism 50 starts to rotate. Thus, the pressing roller 54 is pressed on the eccentric position of the top of the container specimen holder 100. Since the pressing roller 54 is pressed through a spring member 53, it is done stably by a spring power.

The specimen container holder 100 therefore slightly inclines to the left in FIG. 2 and a load concentrates on eccentric position Q of the bottom of the holder 100. Consequently, the holder 100 generates a rotating force in association with the moving force of the belt 13 and thus rotates on its axis together with the specimen container 1.

The control device 60 issues an operation command to the electronic camera 43 of the information reading device 40. The camera 43 moves up and down (camera 43 indicates the camera in a down position) by the lifting/lowering control mechanism and stars to pick up an image. The camera 43 performs a so-called scanning image pickup operation of relatively scanning the sheet attached to the surface of the specimen container 1.

The information obtained by the image pickup operation is coded into bar code information S by the bar-coding device 61 of the control device 60. The bar code information S is supplied to the bar code label issuing and attaching device 70.

On the other hand, when the image pickup operation is completed, the control device 60 is prevented from issuing a control signal to reset the conveyance temporary stop mechanism 32. The specimen container holder 100 restarts to move accordingly. When the holder 100 comes to position P3, the holder sensor 23 senses the labeling ring 102 of the holder 100 and sends the sensed information to the control device 60. Thus, the control device 60 issues an operation control signal to the conveyance temporary stop mechanism 33. The mechanism 33 operates to project the operation rod 30L. The specimen container holder 100 slips on the moving belt 13 and stops in position P3. The specimen container 1 held in the holder 100 that stops in position P3 is carried into the bar code label issuing and attaching device 70 by the robot arm 71.

The bar code label issuing and attaching device 70 issues a label obtained by printing a bar code corresponding to the bar code information S on a given sheet and attaches it to the outer surface of the specimen container 1 carried in by the robot arm 71. The specimen container 1 with the bar code label is returned to the original specimen container holder 100 by the robot arm 71.

When the control device 60 releases the operating state of the conveyance temporary stop mechanism 33, the specimen container holder 100 is carried out as indicated by arrow N in FIG. 1.

(Features of the Embodiment)

[1] A bar code generating apparatus according to an embodiment comprising:

a specimen container holder 100 which holds a container 1 containing a specimen;

a holder conveyance device 10 provided to convey the specimen container holder 100;

a sensor 22 which senses information indicating that the holder conveyance device 10 conveys the specimen container holder 100 to a specific position and outputs the information;

a conveyance temporary stop mechanism 32 which operates based on the information output from the sensor 22 and temporarily stops conveyance of the specimen container holder 100;

a rotation control mechanism 50 which rotates the specimen container holder 100, which is temporarily stopped by the conveyance temporary stop mechanism 32, on an axis of the holder 100;

an electronic camera 43 which picks up an image of recording information on a surface of the specimen container 1 held by the specimen container holder 100 rotated by the rotation control mechanism 50; and a bar-coding device 61 which codes the recording information into a bar code based on data D of the image picked up by the electronic camera 43.

In the bar code generating apparatus described above, the electronic camera 43 picks up an image of characters such as names or handwritten information recorded on the surface of the specimen container 1. Based on the image, the information is coded into bar code information S. It is thus possible to make a bar code label speedily and exactly using the bar code information S.

[2] In the bar code generating apparatus according to item [1], the holder conveyance device 10 includes a belt conveyor mechanism 11.

In the bar code generating apparatus described above, the specimen container holder 100 slips on the belt 13 and stops in a given position. The electronic camera 43 can therefore pick up an image of recording information with accuracy.

[3] In the bar code generating apparatus according to item [2], the conveyance temporary stop mechanism 31 (32, 33) operates in response to an output of the sensor 21 (22, 23) and inserts an operation rod 30L in a forward area in a conveyance direction of the specimen container holder 100 to thereby slip the specimen container holder 100 on the belt 13 and stop the specimen container holder 100 in a specific position thereon.

In the bar code generating apparatus described above, the specimen container holder 100 can be stopped temporarily in a specific position on the belt 13 while the belt conveyor mechanism is operating. Thus, a specimen container holder other than the specimen container holder 100 can continuously be conveyed. Since the conveyor mechanism 11 does not often repeat its start/stop operation, noise due to the start/stop operation can be reduced and so can be damage to the respective components.

[4] In the bar code generating apparatus according to item [3], the rotation control mechanism 50 includes means for depressing an eccentric position of a top of the specimen container holder 100 that slips and stops in the specific position on the belt 13 to incline the specimen container holder 100 and apply a rotating force to the specimen container holder 100 in association with movement of the belt 13.

In the bar code generating apparatus described above, the rotating force can be applied to the specimen container holder 100 simply by depressing an eccentric position of the top of the holder 100. Therefore, no additional rotating power sources need to be provided and thus the configuration of the apparatus can be simplified.

[5] The bar code generating apparatus according to items [1] to [3], further comprises a bar code label issuing and attaching device 70 which issues a bar code label based on bar code information S from the bar-coding device 61 and attaches the bar code label to a given specimen container 1.

What is claimed is:

1. A bar code generating apparatus comprising:

a specimen container holder which holds a container containing a specimen;

a holder conveyance device provided to convey the specimen container holder;

a sensor which senses information indicating that the holder conveyance device conveys the specimen container holder to a specific position and outputs the information;

a conveyance temporary stop mechanism which operates based on the information output from the sensor and temporarily stops conveyance of the specimen container holder;

a rotation control mechanism which rotates the specimen container holder, which is stopped temporarily by the conveyance temporary stop mechanism, on an axis of the holder;

an electronic camera which picks up an image of recording information on a surface of the specimen container held by the specimen container holder rotated by the rotation control mechanism; and a bar-coding device which codes the recording information into a bar code based on data of the image picked up by the electronic camera.

2. The bar code generating apparatus according to claim 1, wherein the holder conveyance device includes a belt conveyor mechanism.

3. The bar code generating apparatus according to claim 2, wherein the conveyance temporary stop mechanism operates in response to an output of the sensor and inserts an operation rod in a forward area in a conveyance direction of the specimen container holder to thereby slip the specimen container holder on the belt and stop the specimen container holder in a specific position thereon.

4. The bar code generating apparatus according to claim 3, further comprising a bar code label issuing and attaching device which issues a bar code label based on bar code information from the bar-coding device and attaches the bar code label to a given specimen container.

5. The bar code generating apparatus according to claim 2, further comprising a bar code label issuing and attaching device which issues a bar code label based on bar code information from the bar-coding device and attaches the bar code label to a given specimen container.

6. The bar code generating apparatus according to claim 1, wherein the rotation control mechanism includes means for depressing an eccentric position of a top of the specimen container holder that slips and stops in the specific position on the belt to incline the specimen container holder and apply a rotating force to the specimen container holder in association with movement of the belt.

7. The bar code generating apparatus according to claim 6, further comprising a bar code label issuing and attaching device which issues a bar code label based on bar code information from the bar-coding device and attaches the bar code label to a given specimen container.

8. The bar code generating apparatus according to claim 1, further comprising a bar code label issuing and attaching device which issues a bar code label based on bar code information from the bar-coding device and attached the bar code lable to a given specimen container.

* * * * *